United States Patent [19]
Park

[11] Patent Number: 5,135,741
[45] Date of Patent: Aug. 4, 1992

[54] ANTIPERSPIRANT PRODUCT

[75] Inventor: Andrew C. Park, Merseyside, England

[73] Assignee: Chesebrough-Pond's USA Co., Division of Conopco, Inc., Greenwich, Conn.

[21] Appl. No.: 587,467

[22] Filed: Sep. 19, 1990

Related U.S. Application Data

[63] Continuation of Ser. No. 725,699, Apr. 22, 1985, abandoned.

[30] Foreign Application Priority Data

Apr. 24, 1984 [GB] United Kingdom ................. 8410403

[51] Int. Cl.$^5$ .................... A61K 7/32; A61K 7/34; A61K 7/38
[52] U.S. Cl. .................... 424/66; 424/68; 514/937
[58] Field of Search .................... 424/66, 68

[56] References Cited

U.S. PATENT DOCUMENTS

| | | | |
|---|---|---|---|
| 2,230,082 | 1/1941 | Montenier | 424/68 |
| 2,236,387 | 3/1941 | Wallace, Jr. et al. | 424/68 |
| 2,571,030 | 10/1951 | Govett et al. | 424/68 |

FOREIGN PATENT DOCUMENTS

| | | | |
|---|---|---|---|
| 1146073 | 5/1983 | Canada | 424/68 |
| 0070517 | 1/1983 | European Pat. Off. | 424/66 |
| 0007406 | 1/1982 | Japan | 424/66 |

OTHER PUBLICATIONS

ICI—Technical Bulletin Antiperspirants and Deodorants, Sep. 1982, pp. 6 and 7.

Primary Examiner—Dale R. Ore
Attorney, Agent, or Firm—Gerard J. McGowan, Jr.

[57] ABSTRACT

A roll-on antiperspirant lotion type composition comprising particles of an antiperspirant agent suspended in a liquid carrier medium wherein the suspending agent is a hydrophobic clay and the liquid medium consists of ethanol or isopropanol or a mixture thereof and 0% to about $3 \times C\%$ by weight of the total liquid medium of one or more liquids less volatile than ethanol or isopropanol provided that where such other liquid comprises a non-polar and water-immiscible liquid such non-polar water-immiscible liquid is present in an amount of not more than about $2 \times C\%$ by weight of the total liquid phase, where C is the percentage weight of the hydrophobic clay in the composition.

5 Claims, No Drawings

ANTIPERSPIRANT PRODUCT

This is a continuation application of Ser. No. 725,699, filed Apr. 22, 1985, now abandoned.

This invention relates to an antiperspirant product.

Many patents have been published during the last 20 years relating to antiperspirant products. These disclose a variety of types of antiperspirant product, differing both as to actual composition as well as product type. Common product types are the aerosol, roll-on and stick forms of antiperspirant. The actual composition itself, which may be applied from the aerosol, roll-on or stick applicator, can be of various types which include the two commonly used forms in which the antiperspirant active ingredient is present in solution in an appropriate solvent, on the one hand, or is present in powder form, on the other hand. The latter type are often referred to as powder suspensions since the powder is invariably present dispersed in a suitable liquid carrier medium, which medium will contain a thickening agent in order to produce a sufficiently stable suspension.

There are many antiperspirant products available on the world market today of the different kinds referred to above. Those of the powder suspension type are predominantly limited to use with an aerosol or stick applicator, with, it is believed, only a very small number of products being in the form of a roll-on lotion. In these roll-on products the powdered antiperspirant active agent is suspended in a silicone or mixture of silicones and they have compositions as generally disclosed in British Patent No. 2,018,590 (Gillette) and European Patent No. 28 853 (Procter & Gamble).

The formulation of a stable effective and acceptable suspension-type product in lotion form does present difficulties and there are relatively few patents concerned with such products. The first of these was British Patent No. 1,192,021 (Unilever) which disclosed the broad concept of suspending the active antiperspirant agent in powder form in a normally liquid substantially anhydrous volatile medium so overcoming a disadvantage of aqueous solution products which give a tacky feeling during drying. In British Patent No. 2,018,590 (Gillette), referred to above, the volatile medium used is a cyclic silicone. In European Patent No. 28,853 (Procter & Gamble), also mentioned above, the liquid vehicle is a mixture of a volatile cyclic or linear polydimethylsiloxane and a non-volatile emollient which is a silicone, liquid paraffin or mixture thereof. Canadian Patent No. 1,119,960 (Warner-Lambert) concerns an improvement of the volatile cyclic silicone formula, the improvement residing in the inclusion of various suspension stabilisers. In U.S. Pat. No. 4,435,382 (Shin et al) the active antiperspirant agent is an aluminium or aluminium/zirconium salt glycine complex which is suspended in anhydrous ethanol, the exemplified compositions employing a combination of hyrophobic and hydrophilic emollients so as to give products having low staining potential. Japanese Patent Publication 7406/1982 is also concerned with the obtaining of a quick dry product giving reduced stickiness and further aims to reduce contact with clothes while the product is still wet. The liquid system contains little or no alcohol or water and consists almost entirely of non-polar solvents, the main ingredients being silicones or hydrocarbons having a boiling point of from 90° to 110° C., for example hexamethyldisiloxane or the isoparaffin hydrocarbon mixture available commercially under the trade name ISOPAR C. The roll-on composition preferably contains up to 40% by weight of the composition of a cyclic polydimethylsiloxane and also comprises a Bentone suspending agent which is preferably pre-dispersed in isopropyl myristate while additional isopropyl myristate may be included.

The patents referred to above have, in the main, not been concerned with the actual antiperspirant efficacy, i.e. how effective the respective product is in reducing the production of sweat when applied to the axillae. However, British Patent No. 2,018,590 (Gillette) discloses that by omitting, or keeping to a low level, other hydrophobic ingredients less volatile than the cyclic silicone, an antiperspirant effectiveness matching that of an aqueous solution of the antiperspirant agent is obtained. In contrast, European Patent No. 28,853 (Procter & Gamble) discloses that addition of a non-volatile silicone or liquid paraffin to a volatile silicone carrier liquid enhances antiperspirant efficacy.

Generally speaking, in their attempts to formulate products having high efficacy, those skilled in the art have tended hitherto to concentrate on the development of active agents which themselves intrinsically have high efficacy, i.e. on a weight for weight basis give greater reductions in sweat production than already known actives when applied to the axillae from otherwise similar formulations.

Examples of such more recently developed materials are the now well-known zirconium-aluminium chlorhydroxides and their complexes with glycine. These are available commercially, for example under the trade mark REZAL from Reheis Chemical Co. Such complexes applied in aqueous solution produce sweat reductions, in a standard test procedure described in detail later in this specification, of about 40–45%. Furthermore, Applicants have found that these complexes when suspended in a volatile cyclic silicone, such as VS 7207 (from Union Carbide) or DC 344 (from Dow Corning), or in a linear volatile silicone such as hexamethyldisiloxane also give sweat reductions of about 40–45%.

In contrast to these findings Applicants were surprised to discover that when the same zirconium aluminium glycine complexes were suspended in ethanol with the aid of a hydrophobic hectorite clay a sweat reduction of about 60% was obtained. Such a degree of sweat reduction is very high indeed.

Applicants believe that in improving the performance of any given active with reference to its aqueous solution counterpart it is important that the active agent be in solid particulate form. This does not appear to have been recognised hitherto although products in which the active antiperspirant agent is in solid form are known as indicated earlier in this specification.

Of course, in order to produce a commercially viable product of the suspension type, the active ingredient has to remain stably suspended for a considerable period of time. It is in this respect that the products of Applicants' previous British Patent No. 1,192,021 are unsatisfactory because the active agent referred to in the patent, i.e. aluminium chlorhydrate, gradually dissolves in the alcohol carrier medium.

However, Applicants have now found it possible to produce a stable suspension of aluminium chlorhydrate in anhydrous ethanol or isopropanol, as will be described more particularly hereinafter. When employing such findings in the production of a stable suspension of the more active form of aluminium chlorhydrate produced by procedures described in U.S. Pat.

No. 4,359,456 (Gosling et al), using as the sole suspending agent the readily water-soluble cellulosic material known as KLUCEL M referred to in said British Patent No. 1,192,021, a sweat reduction also of around 40% was obtained. However, it was surprising to find that when a hydrophobic clay such as Bentone 38 was used as the suspending agent in place of the cellulosic material a substantially higher sweat reduction of about 55-60% was obtained. These results show that the efficacy of such systems is dependent upon the choice of the structuring agent employed.

A yet further finding made by the applicant is that concerning the effect on the antiperspirant efficacy of the product of the presence of non-volatile oils, whose inclusion may be desirable to impart emollient properties as described in, for example, U.S. Pat. No. 4,435,382 (Shin et al). We have found that the antiperspirant efficacy of suspensions of antiperspirant agent in anhydrous ethanol or isopropanol thickened with a hydrophobic clay can be reduced by oily additives less volatile than ethanol or isopropanol and that the permissible amount of additive without substantial loss of efficacy is dependent on the amount of the clay suspending agent. The permissible amount of any non-volatile component of the liquid phase also depends on whether such component is hydrophilic or hydrophobic.

These findings have enabled the Applicants to define a novel antiperspirant composition of the lotion type for application to the skin from a roll-on applicator having an antiperspirant efficacy superior to that of an aqueous solution of an antiperspirant agent.

According to the present invention there is provided an antiperspirant composition of the lotion type for applying to the skin from a roll-on dispenser which comprises about 5 to 40% by weight of an antiperspirant agent in the form of fine particles suspended in about 50 to about 92% by weight of the composition of an anhydrous normally liquid medium by means of a suspending agent, which composition is characterised in that:
(i) the suspending agent comprises a hydrophobic clay in an amount of 3 to 15% by weight of the composition, and
(ii) the liquid medium consists of ethanol or isopropanol or a mixture thereof and 0% to about $3 \times C$. % by weight of the total liquid medium of one or more liquids less volatile than ethanol or isopropanol provided that where such other liquid comprises a non-polar and water-immiscible liquid such non-polar water-immiscible liquid is present in an amount of not more than about $2 \times C$. % by weight of the total liquid phase, where C. is the percentage weight of the hydrophobic clay in the composition.

In the antiperspirant roll-on lotion product of the invention the antiperspirant agent is in particulate form suspended in the liquid carrier medium. Examples of suitable antiperspirants in powder form are aluminium sulphate; aluminium chlorhydroxide; basic aluminium bromide, zirconyl chloride; zirconyl hydroxide; zirconyl hydroxychloride; complexes of aluminium hydroxide, zirconyl chloride and aluminium chlorhydroxide; complexes of aluminium hydroxide, zirconyl hydroxychloride, and aluminium chlorhydroxide; complexes of dihydroxyaluminium glycinate, zirconyl chloride and/or zirconyl hydroxychloride and aluminium chlorhydroxides; complexes of zirconyl chloride and/or zirconyl hydroxychloride and aluminium chlorhydroxide; complexes of zirconyl chloride and/or zirconyl hydroxychloride with aluminium chlorhydroxide and an amino acid, such as glycine; and mixtures of two or more of the above. Most preferred materials are those which have a high antiperspirant efficacy. One class of such materials are the aluminium zirconium chlorhydrate complexes. Examples are aluminium zirconium trichlorhydrate, aluminium zirconium tetrachlorohydrate and aluminium zirconium pentachlorohydrate (these are CTFA generic names). These compounds may be combined with glycine to give for example the compounds known under the CTFA generic names aluminium zirconium trichlorohydrex-GLY and aluminium zirconium tetrachlorohydrex-GLY. Methods for preparing aluminium zirconium chlorhydrates are described in a number of patents, for example U.S. Pat. Nos. 4,028,390 (Armour) and 3,792,068 (Procter & Gamble) the disclosures of which are incorporated herein by reference. Suitable aluminium zirconium chlorhydrate powders for use in the antiperspirant compositions of this invention are available from the Reheis Chemical Company under the trade names REZAL 36GP and REZAL 67P (REZAL is trade mark) and from Wickhen Products, Incorporated under the trade names WICKENOL 369 and WICKENOL 379 and WICKENOL 373 (WICKENOL is a trade mark). Other preferred antiperspirant active materials of high efficacy are the special active forms of basic aluminium chloride which have a particular distribution of polymeric species in aqueous solution and obtainable by procedures described in U.S. Pat. No. 4,359,456 (Gosling et al). Similar processes for making highly active forms of aluminium chlorhydrate involving the ageing of aluminium chlorhydrate in an aqueous medium are described in British Patent Specification No 2,048,229 (Gillette). Other suitable materials are described in British Patent Specification No. 2,144,992 (Gillette). The disclosures of the Gosling et al and Gillette patents are incorporated herein by reference. The antiperspirant agent may also be a urea or glycine complex of aluminium chlorhydrate prepared as described in European Patent No. 6738 (Unilever) and British Patent No. 1,597,497 (Unilever), respectively, the disclosure of which patents are incorporated herein by reference.

The amount of the antiperspirant agent present in the composition will in general be within the range 5 to 40% by weight, preferably 8 to 35% by weight, more usually 10 to 30% by weight.

The suspending agent of the antiperspirant composition of the invention for suspending the particles of the antiperspirant in the liquid carrier phase is a hydrophobic clay. Particularly suitable clays are the hydrophobically treated smectite clays. Smectite clays are those characterised by having an expanding lattice. Examples of these clays include the montmorillonites, hectorites, and colloidal magnesium aluminium silicates.

Montmorillonite is colloidal, hydrated aluminium silicate obtained from bentonite of which it is the predominant constituent. A detailed discussion of bentonites can be found in the Kirk-Othmer Encyclopedia of Chemical Technology, 2nd Edition, Vol. 3 (1964) pp. 339-360, published by Interscience Publishers, which is incoporated herein by reference.

Hectorite, also a smectite clay, differs from montmorillonite in that there is almost a complete substitution of aluminium in the lattice structure of montmorillonite by magnesium and in addition, the presence of lithium and fluorine.

The magnesium aluminium silicates are complexes of colloidal magnesium aluminium silicate richer in magnesium than aluminium. The hydrophobically treated magnesium aluminium silicates are commercially available under the name Veegum PRO from the R T Vanderbilt Co.

Preferred suspending agents for use in the present invention are hydrophobic clays available under the trade name of "Bentone". Bentones are prepared by reacting a suitable clay in a cation exchange system with an amine. Different amines are reacted to obtain a variety of Bentones, which may also differ in proportions of Si, MgO and $Al_2O_3$. Examples of useful "Bentone" suspending agents are "Bentone-27", which is a stearaluminium hectorite; "Bentone-34", which is quaternium 18 bentonite; "Bentone-38", which is quaternium 18 hectorite; and "Bentone-14" which is a clay-extended quaternium 18 hectorite, all of which have a particle size of below 5 microns and are commercially available in USA from NL Industries Inc. Other suitable "Bentone" clays are Bentone SD1 and Bentone SD2.

Yet further suitable clays are those hydrophobically treated smectite clays available under the trade names Perchem and Tixogel. Specific examples are Perchem clays 44, 97 and 108 and Tixogel VZ. Also suitable is the hydrophobically modified attapulgite clay available under the name Perchem DMA. Perchem clays are sold by Perchem Limited of Harlow, Essex, Great Britain and Tixogel clays by Production Chemicals Limited of Stockport, Cheshire, Great Britain.

The liquid carrier medium of the antiperspirant composition of this invention consists essentially of anhydrous ethanol or isopropanol.

However, other liquids may form part of the liquid carrier medium of the roll-on antiperspirant product of the invention. Such additional liquids may be incorporated to give emollient cosmetic benefits and may be either hydrophilic or hydrophobic liquids. It has been discovered that the amount of emollient oil that can be permitted without significant loss of antiperspirant efficacy is dependent upon the amount of hydrophobic clay suspending agent that is present in the composition as well as on the nature of the oil itself. Thus in the antiperspirant products of the invention the amount of oil present in the liquid phase is 0% to $3 \times C$. % by weight of the liquid phase provided that where a non-polar water-immiscible liquid is included the amount of such liquid does not exceed $2 \times C$. % by weight of the liquid phase, where C. is the percentage weight of the hydrophobic clay in the antiperspirant composition.

The emollient liquid may be a polar liquid such as (1) a water-miscible polyoxyalkylene glycol or a water-miscible partial butyl ether thereof; (2) hexylene glycol; (3) a $C_1$-$C_4$ alkyl monoether of a simple or condensed $C_2$-$C_4$ alkylene glycol for example dipropylene glycol monomethyl ether; or (4) 2-ethyl-1,3-hexane diol. Such materials (1), (2), (3) and (4) have previously been suggested for use in powder suspension aerosol antiperspirants in, respectively, British Patents 1 300 260, 1 329 011, 1 369 872 and 1 409 533 (all to Unilever) from which patents more information concerning particularisation of these groups of carrier media can be obtained and whose disclosures are incorporated herein by reference. Other commercially available hydrophilic materials which are suitable are Pluronics (e.g. Poloxamer 101, Poloxamer 105, Poloxamer 181, Poloxamer 182), Carbowaxes (e.g. PEG-4, PEG-8, PEG-12}, Witconol APEM (PPG-3 Myreth-3), Witconol APES (PPG-9 Steareth-3), Standamul OXL (PPG-10 Ceteareth-20), Procetyl AWS Modified (PPG-8 Ceteth-2). Glycols and their citrate, lactate and tartrate esters as taught in Canadian Patents 1 121 728; 1 121 729 and 1 121 730 can also be used. Hydrophilic materials which are especially useful are the dimethicone copolyols which are polymers of dimethylsiloxane with polyoxyethylene and/or polyoxypropylene side chains. Examples of these are SILWET L-720, L-7600 and L-7610 from Union Carbide, Silicone 190 and 193 surfactants both from Dow Corning and ABIL B 8842, 8843 and 8851 from Goldschmidt. These dimethicone copolyols are also referred to in the literature as polyalkylene oxide modified dimethylpolysiloxanes, as silicone glycol copolymers and as polysilicone polyether copolymers. Dimethyl isosorbide is a further example of a suitable hydrophilic liquid.

Examples of non-polar water-immiscible liquids that may be present in minor proportion are the linear volatile silicones having 3 to 6 carbon atoms such as hexamethyl disiloxane, the cyclic volatile silicones having 3 to 6 carbon atoms such as the tetramer and pentamer and mixtures thereof, paraffin oils, fatty acid esters such as isopropyl myristate and dibutyl phthalate, and polyoxypropylene fatty ethers such as Fluid AP.

The liquid carrier medium will usually amount to from 50 to 92% by weight, preferably 50 to 80% by weight, of the antiperspirant composition.

It may be considered desirable to include in the liquid carrier medium a proportion of hydrophilic or hydrophobic oil (which will be less volatile than ethanol or isopropanol). As stated these oils can impart emollient properties and they may also reduce the whiteness of the deposit of the antiperspirant powder, which deposit remains after evaporation of the ethanol or isopropanol. The discoveries made as referred to herein permit, by usage of amounts of clay of say 5-15%, preferably 6-12%, by weight of the composition, usage of amounts of emollient oil that are adequate to provide an emollient effect and overcome the whiteness problem referred to without significant loss of antiperspirant efficacy. Consequently, an especially useful range of products according to this invention comprise 6-12% hydrophobic clay and an amount of emollient oil of at least $0.5 \times C$. % by weight of the liquid phase, where C. is the weight percentage of the hydrophobic clay present in the composition.

In the antiperspirant products of the invention it is desirable that the particulate antiperspirant agent has a high degree of insolubility in the ethanol or isopropanol. The antiperspirant agents referred to above have varying degrees of insolubility in ethanol and isopropanol, being generally more prone to slow dissolution in ethanol, even anhydrous ethanol, than in anhydrous isopropanol. The glycine complexes that have been referred to usually pass very much more slowly into solution than do the uncomplexed materials. Nevertheless, it is desirable to reduce the rate of dissolution for all the antiperspirant active agents.

In co-pending Park application Ser. No. 6/725,681, entitled "Method for Inhibiting The Dissolution of Antiperspirant Compounds In Alcohols" and filed concurrently herewith, the disclosure of which is incorporated herein by reference, there is described a method of inhibiting the dissolution in anhydrous ethanol or isopropanol of a powdered aluminium-containing basic halide antiperspirant agent which comprises incorporating in the ethanol or isopropanol an amount effective to inhibit said dissolution of an alcohol soluble or alcohol-insoluble dissolution-inhibiting compound selected from the group consisting of compounds having a basic nitrogen function and compounds having a basic oxygen function.

Examples of compounds having a basic nitrogen function are urea and thiourea; amino acids for example glycine, alanine, taurine, serine, sarcosine, valine, leucine, proline, methionine, threonine, arginine, ornithine, lysine, lysine monohydrochloride, glutamic acid monomethyl ester (which amino acids include the neutral amino acids and the basic amino acids); and the $C_1$–$C_{20}$ alkylamines and hydroxyalkylamines, for example triethylamine, mixed $C_{13}/C_{15}$ alkylamine and 2-amino-2-methyl-propan-1-ol.

Examples of compounds having a basic oxygen atom are inorganic bases such as the hydroxides of the alkali metal and the alkaline-earth metals and ammonium hydroxide, including sodium hydroxide, potassium hydroxide, lithium hydroxide, calcium hydroxide and magnesium hydroxide, as well as the basic metallic oxides, for example zinc oxide and lanthanum oxide; and the alkali metal salts and alkaline-earth metal salts of inorganic acids, for example sodium carbonate, sodium tetraborate, sodium thiosulphate and dipotassium hydrogen orthophosphate, and of $C_1$–$C_{20}$ organic carboxylic acids for example sodium acetate, trisodium citrate, sodium n-octanoate and sodium stearate.

An appropriate amount of the anti-dissolution agent is simply incorporated into the alcohol prior to the addition of the powdered antiperspirant agent or together with it. It is less satisfactory to include it afterwards.

The amount of the anti-dissolution agent is that which is effective to inhibit dissolution of the powdered antiperspirant compound in the alcohol. The amount required will depend on the particular inhibitor employed. Generally speaking a satisfactory amount will be from about 0.1 to about 25% by weight of the ethanol or isopropanol. The amount of urea, thiourea or amino acid will generally be in the range of about 0.5 to about 25% by weight of the alcohol although in practice any amount can be included which is consistent with an acceptable product. The alkylamines and hydroxyalkylamines are used in an amount of about 0.5 to about 4% by weight of the alcohol. The alkali metal inorganic bases and ammonium hydroxide are suitably used in amounts of about 0.1 to about 2% by weight of the alcohol and other inorganic bases, basic oxides and inorganic acid salts in amounts of about 0.5 to 10% by weight of the alcohol. The salts of the $C_1$–$C_{20}$ carboxylic acids may be used in an amount of about 1 to about 20% by weight of the alcohol.

In said copending application there is also disclosed a method of inhibiting the dissolution in anhydrous ethanol or isopropanol of a powdered aluminium-containing basic halide antiperspirant agent which comprises incorporating in the ethanol or isopropanol an amount effective to inhibit said dissolution of a particulate alcohol-insoluble inorganic drying agent. Examples of suitable inorganic drying agents are anhydrous sodium sulphate and molecular sieves, for example the material known as Molecular Sieve Type 3A. Other inorganic drying agents are described in Kirk-Othmer's Encyclopedia of Chemical Technology, 2nd Edition, Vol 7 (1965) pages 378 to 396, the disclosure of which is incorporated herein by reference. Any drying agent which is compatible with the alcohol is suitable. Effective amounts of the drying agent for the inhibition of dissolution of the antiperspirant agent will be found in the range 1 to 20% by weight of the alcohol.

A further method of rendering aluminium- and zirconium-containing antiperspirant agents such as those described above substantially insoluble in hydrophilic liquids, especially ethanol and isopropanol, is by adjusting the water content of the active agent to a suitably low level. In this way substantial insolubility can be achieved without any significant loss of antiperspirant efficacy (which may occur if an active agent is excessively dehydrated). The optimum degree of drying may differ for different materials. Drying to a total water content in the range about 7 to about 11% by weight is preferred, this range being particularly appropriate for activated aluminium chlorhydrate. Thus, according to an aspect of the present invention there is provided for use in the lotion antiperspirant composition of the invention an aluminium chlorhydrate of enhanced activity as defined in U.S. Pat. No. 4,359,456 (Gosling et al) of the formula $Al_2(OH)_{6-y}Cl_y \cdot nH_2O$ where the ratio 2:y is 0.5 to 6, more preferably 1.5 to 4.0, most preferably 1.95 to 2.1 and n is about 0.7 to about 1.2.

Substantial insolubility of the antiperspirant agent in the liquid medium may be achieved by use of a combination of the above methods, e.g. by using an antiperspirant agent which is, for instance, a pre-formed complex with glycine, and including an anti-dissolution agent such as urea in an ethanolic liquid medium, or by using a partially dried antiperspirant agent (for example an aluminium chlrohydrate having a water content of less than 1.8 moles of water of hydration) in combination with an anti-dissolution agent.

It is common practice to include small amounts of perfume oils in antiperspirant compositions of the types to which this invention relates. Preferred perfume oils are those having deodorant activity as described in GB-PS 2,013,493A. Perfume oils comprise part of the liquid medium of the composition. Other possible additional ingredients are bactericides and preservatives.

In the following part of this specification references are made to the antiperspirant efficacy of various products. Before giving details of the composition of these products the test procedure carried out to evaluate their antiperspirant efficacy will first be described. The test procedure involves subjecting human volunteers to thermal stress and gravimetric determination of axilla sweat.

Subjects

A panel of up to 60 women who use no antiperspirant for the 14 days before the test.

Hot Room

Temperatures 40° C.±2° C.; relative humidity 40%±5%.

Products

Two products of which one is designated the control. The panel is divided into two equal groups. One group receives the test treatment on the left axilla and the control treatment on the right, while the second group receives them the other way round.

Control Product

Placebo deodorant. This was an aerosol product comprising 25% ethanol, 0.6% isopropyl myristate, 0.3% perfume, and 74.1% propellant (1:1 mixture of Propellants 11 & 12).

Product Application

The operator conducting the test applies the test product in the normal way so as to deposit an appropriate quantity of product e.g. on average about 300 mg of product.

Sweat Collection

Absorbent cotton pads are used to collect the sweat. On entering the hot room each panellist is subjected to a 40 minute 'warm-up' period, during which no sweat is collected. Sweat is then collected for a 20 minute period and sweat weight determined.

Test Design

Subjects attend daily for 3 consecutive days. They receive one treatment with the products on each of the first three days. Following product application on the third day, the panellist is subjected to a hot room sitting and sweat collection.

Analysis of Data

The statistical treatment includes an analysis of variance which allows for panellist side and product effects. The efficacy is calculated from the geometric mean weight of sweat collected from the axillae treated with each product using the formula $$\% \text{ reduction} = 100 \frac{(C - T)}{C}$$

where C. is the geometric mean sweat weight from the axillae treated with the control product and T is the geometric mean sweat weight from the axillae treated with the test product where a correction has been made for the side effect.

Significance is calculated by applying Student's t-test to the logarithmically transformed weights.

Tests with the compositions of Table I show the effect on the antiperspirant efficacy of a product (Composition A) containing anhydrous ethanol as the carrier medium of replacing part of the ethanol by another liquid (Compositions B to L). The antiperspirant efficacy data are given in Table II.

TABLE I

| Component | Composition: | A | B | C | D | E | F | G | H | J | K | L |
|---|---|---|---|---|---|---|---|---|---|---|---|---|
| | | | | | | % | | | | | | |
| Rezal 36GP[1] | | 25.0 | 24.0 | 25.0 | 25.0 | 25.0 | 25.0 | 25.0 | 25.0 | 25.0 | 25.0 | 25.0 |
| Bentone 38 | | 10.0 | 2.5 | 10.0 | 10.0 | 10.0 | 10.0 | 10.0 | 10.0 | 10.0 | 10.0 | 3.5 |
| Bentone 27 | | — | 1.0 | — | — | — | — | — | — | — | — | — |
| Aerosil 200[2] | | — | 1.5 | — | — | — | — | — | — | — | — | — |
| Fluid AP[3] | | — | 15.0 | 7.5 | 15.0 | 15.0 | — | — | — | — | — | — |
| VS 7207[4] | | — | — | — | — | — | 15.0 | 32.0 | — | — | — | — |
| DPGME[5] | | — | — | — | — | — | — | — | 15.0 | 32.0 | — | — |
| Propylene glycol | | — | — | — | — | — | — | — | — | — | 15.0 | 15.0 |
| Urea | | — | — | — | — | 2.6 | — | — | — | — | 2.6 | 3.0 |
| Ethanol (anhydrous) | | 64.0 | 55.92 | 56.5 | 49.0 | 46.4 | 49.0 | 32.0 | 49.0 | 32.0 | 46.4 | 52.5 |
| Perfume | | 1.0 | 0.08 | 1.0 | 1.0 | 1.0 | 1.0 | 1.0 | 1.0 | 1.0 | 1.0 | 1.0 |

TABLE II

| | Composition | | | | | | | | | | |
|---|---|---|---|---|---|---|---|---|---|---|---|
| | A | B | C | D | E | F | G | H | J | K | L |
| % Sweat Reduction | 58 | 39 | 52 | 48 | 46 | 48 | 50 | 54 | 42 | 58 | 45 |
| Equivalent % Sweat Reduction of Composition A[6] | — | 57 | 55 | 53 | 60 | 55 | 56 | 55 | 55 | 56 | 55 |
| % Decrease[7] | — | 42 | 7 | 10 | 35 | 16 | 14 | 2 | 29 | −5 | 22 |
| Significance of Decrease[8] | — | S | N | S | S | S | S | N | S | N | S |

[1]Aluminium zirconium tetrachlorohydrex glycine complex available from Reheis Chemical Company. It has a particle size of less than 53 microns (at least 98.5% less than 44 microns).
[2]Fumed silica
[3]A hydrophobic oil, a product of Union Carbide Corporation; its CTFA name is PPG-14 Butyl Ether
[4]A cyclic polydimethylsiloxane comprising mainly tetramer and available from Union Carbide.
[5]Dipropylene glycol methyl ether available from Dow Chemical under the trade name Dowanol DPM.
[6]The equivalent percentage sweat reduction of Composition A is that sweat reduction obtained when using Composition A in such a manner that the same average weight of Rezal 36 GP is deposited by Composition A as by the test product - thus in this comparison account is taken of variations in the amount of active applied to the axillae.
[7]The percentage decrease is calculated from the percentage sweat reduction of the product ($SWR_p$) and the equivalent percentage sweat reduction of Composition A ($SWR_{AEQ}$) using the expression
$$\frac{(SWR_{AEQ} - SWR_p) \times 100}{100 - SWR_{AEQ}}$$
[8]S means significantly different at the 95% level, NS means not significantly different.

In the tests with Compositions C. and D the control product used was Composition A. The sweat reductions of Compositions C. and D, respectively, were calculated from the measured decreases with respect to Composition A and the known sweat reduction of Composition A.

The effect of the hydrophobic liquid Fluid AP on antiperspirant efficacy is illustrated by the results obtained with Compositions B to E. For each of compositions B, D and E the weight of the Fluid AP expressed as a percentage of the total liquid medium exceeds 2×C. % where C. is the weight of the Bentone clay in the respective composition. Only in Composition C where this percentage is less than 2×C. %, and thus the product is one in accordance with the present invention, is there no significant decrease in the antiperspirant efficacy of the product. Composition B is based on Examples 8 and 9 of U.S. Pat. No 4,435,382 (Shin et al).

Other tests have shown that Aerosil does not affect efficacy when combined with Bentone.

A similar effect is shown in the case of Compositions F and G where in each case the amount of hydrophobic silicone oil in the composition expressed as a percentage of the total liquid phase of the composition is more than 2×C. % where C. is the percentage weight of the clay thickener. In each case the inclusion of the silicone oil resulted in a significant decrease in the efficacy of the composition.

In the case of Compositions H and J the effect of adding a hydrophilic oil is demonstrated. Composition H is a composition in accordance with the present invention wherein the amount of the hydrophilic oil expressed as a percentage of the weight of the total liquid medium is less than 3×C. % where C. is the weight of the hydrophobic clay thickener. The antiperspirant efficacy of Composition H was not significantly different from that of Composition A. In contrast, however, in the case of Composition J in which the amount of the hydrophilic oil, when expressed as a percentage of the weight of the liquid medium exceeded 3×C. %, the inclusion of the oil resulted in a significant decrease in antiperspirant effectiveness.

For the Compositions K and L, both of which include a proportion of the hydrophilic material propylene glycol, it is again demonstrated that for an amount of a hydrophilic oil less than 3×C. % (again expressing the oil as a percentage by weight of the total liquid components), as in Composition K which is in accordance with this invention, there is no significant loss in antiperspirant efficacy, whereas there was a significant decrease in effectiveness in the case of Composition L for which the amount of hydrophilic oil exceeded the 3×C. % value.

Other formulae tested are given in Table III. The results indicate the relatively inferior results obtained using thickening agents other than the hydrophobic clays and when using a silicone fluid instead of ethanol or isopropanol.

TABLE III

| Component | Composition: | M | N | P | Q | R | S |
|---|---|---|---|---|---|---|---|
| ACH[1] | | — | 25.0 | 30.0 | — | — | — |
| Rezal 36 GP | | 25.0 | — | — | 25.0 | 25.0 | 25.0 |
| Bentone 38 | | — | 10.0 | — | 5.0 | 10.0 | — |
| Aerosil 200 | | — | — | 2.0 | — | — | — |
| Klucel M[2] | | 0.74 | — | — | — | — | — |
| Veegum Regular[3] | | — | — | — | — | — | 10.0 |
| Ethanol (anhydrous) | | 73.26 | 60.6 | 67.5 | 2.0 | — | 64.0 |
| VS 7207 | | — | — | — | 66.5 | — | — |
| HMDS[4] | | — | — | — | — | 64.0 | — |
| Water | | — | — | — | 0.5 | — | — |
| Perfume | | 1.0 | 1.0 | 0.5 | 1.0 | 1.0 | 1.0 |
| Urea | | — | 3.4 | — | — | — | — |
| % Sweat Reduction | | 26 | 42 | 19 | 45 | 44 | 42 |

[1]Aluminium chlorhydrate
[2]Hydroxypropylcellulose
[3]A magnesium aluminium silicate clay not organically modified to render it hydrophobic
[4]Hexamethyldisiloxane available for example from Dow Corning under the name Dow Corning DC 200 fluid, 0.65 cs.

By comparing the result for Composition M with that for Composition A of Table I it is shown that the use of a hydrophobic clay thickening agent gives a more effective product than a comparable product using a cellulosic thickener.

By comparing Compositions N and P which both employ aluminium chlorhydrate as the active agent it was found that the product thickened with the hydrophobic clay was far superior in efficacy to the one thickened with a fumed silica.

In composition Q a cyclic volatile silicone constituted the major part of the liquid medium of the product. The efficacy of this product was considerably less than that of the similar Composition A using ethanol as the liquid vehicle (see Table II). On testing the commercial product called DRY IDEA, also based on an aluminium zirconium glycine complex, Bentone clay and volatile silicone, a value of 38% was obtained for the sweat reduction.

Composition R also shows that a poor result is obtained using a linear volatile silicone to constitute the liquid medium of the product.

Composition S shows that a poor result is obtained when using a clay which has not been organically modified to render it hydrophobic.

The following further examples of antiperspirant roll-on lotions illustrate the invention. Percentages are by weight.

| Examples: | 1 | 2 | 3 | 4 | 5 | 6 | 7 | 8 |
|---|---|---|---|---|---|---|---|---|
| AACH[1] | 25.0 | — | 25.0 | — | — | 20.0 | — | 10.0 |
| AACH/Urea complex[2] | — | — | — | 25.0 | — | — | — | — |
| Rezal 36GP | — | 25.0 | — | — | 25.0 | — | 20.0 | 15.0 |
| Ethanol (anhydrous) | 60.8 | 64.0 | — | 64.0 | — | 67.4 | 70.0 | — |
| Isopropyl alcohol | — | — | 62.7 | — | 64.0 | — | — | 60.8 |
| Bentone 38 | 10.0 | 10.0 | 10.0 | 10.0 | — | 8.0 | 8.0 | — |
| Bentone 27 | — | — | — | — | 10.0 | — | — | 10.0 |
| Perfume | 1.0 | 1.0 | 1.0 | 1.0 | 1.0 | 1.0 | 1.0 | 1.0 |
| Urea | 3.2 | — | 1.3 | — | — | 3.6 | 1.0 | 3.2 |

| Examples: | 9 | 10 | 11 | 12 | 13 | 14 |
|---|---|---|---|---|---|---|
| AACH[1] | 25.0 | — | — | — | — | — |
| AACH/Urea complex[2] | — | 25.0 | — | 25.0 | 20.0 | — |
| Rezal 36GP | — | — | 25.0 | — | — | — |
| ACH | — | — | — | — | — | 25.0 |
| Ethanol (anhydrous) | 51.3 | 58.0 | 63.0 | 50.0 | 51.5 | 61.5 |
| HMDS | — | — | 5.0 | 4.0 | — | — |
| VS 7207 | 10.0 | — | — | 5.0 | — | — |
| DPGME | — | 8.0 | — | 5.0 | 18.0 | — |
| Bentone 38 | 10.0 | 7.0 | 6.0 | 10.0 | 9.0 | 10.0 |
| Perfume | 1.0 | 1.0 | 1.0 | 1.0 | 1.0 | 1.0 |
| Urea | 2.7 | 1.0 | — | — | 0.5 | 2.5 |

| Examples: | 15 | 16 | 17 | 18 |
|---|---|---|---|---|
| AACH[1] | — | — | — | 25.0 |
| Rezal 36GP | 25.0 | 25.0 | 25.0 | — |
| Ethanol (anhydrous) | 69.0 | 66.0 | 66.8 | 60.6 |
| Bentone 38 | 5.0 | 4.2 | 3.4 | 10.0 |
| Perfume | 1.0 | 1.0 | 1.0 | 1.0 |
| Urea | — | 3.8 | 3.8 | 3.4 |

[1]Spray-dried powder of an activated aluminium chlorhydrate prepared according to U.S. Pat. No. 4 359 456. It had a particle size of less than 75 microns. It has a Band III percent Aluminium Value of greater than 20%. The AACH employed in Example 18 was dried to 1.1 moles of water.
[2]This is a pre-formed complex of urea and an activated aluminium chlorhydrate (AACH) prepared by codissolving AACH and urea (mole ratio 2:1) in water and spray drying the solution.

The products employed in the above tests and those of the Examples are made by shearing the suspending agent in the liquid component or mixture of the liquid components, excluding the perfume, until fully dispersed. When urea is present this is pre-dissolved in the alcohol. The antiperspirant powder and perfume are then added and dispersed by further high shear mixing. The product is then filled into roll-on dispensers.

The results of tests conducted with each of the products of Example 1 to 4 and 15 to 18 are as follows.

| Product | % Sweat Reduction |
|---|---|
| Example 1 | 58 |
| Example 2 | 58 |
| Example 3 | 53 |
| Example 4 | 54 |
| Example 15 | 62 |
| Example 16 | 62 |

| Product | % Sweat Reduction |
| --- | --- |
| Example 17 | 54 |
| Example 18 | 60 |

The products of all of Examples 1 to 18 are stable antiperspirant lotions which dry quickly to form a structured, tenacious film on the skin. The urea present in various of the products acts as an anti-dissolution agent enhancing stability of the active antiperspirant agent. It can also improve the structure imparted by the Bentone.

In a comparative test with a product having a composition similar to that of Example 3 and comprising 25% AACH, 0.74% Klucel, 71.78% isopropyl alcohol, 1.0% perfume and 1.48% urea, a sweat weight reduction of 40% was obtained. This test confirms that use of a thickening agent other than a hydrophobically modified clay gives inferior results.

What is claimed is:

1. An antiperspirant composition of the lotion type for applying to the skin from a roll-on dispenser which comprises about 5 to 40% by weight of an antiperspirant agent in the form of fine particles suspended in about 50 to about 92% by weight of the composition of an anhydrous normally liquid medium by means of a suspending agent, and wherein:
   (i) the suspending agent comprises a hydrophobic clay in an amount of 10% by weight of the composition, and
   (ii) the liquid medium consists of ethanol or isopropanol or a mixture thereof and 0% to about 3° C. % by weight of the total liquid medium of one or more liquids less volatile than ethanol or isopropanol provided that where such other liquid comprises a non-polar and water-immiscible liquid such non-polar water-immiscible liquid is present in an amount of not more than about 2° C. % by weight of the total liquid phase, where C. is the percentage weight of the hydrophobic clay in the composition.

2. An antiperspirant composition of the lotion type for applying to the skin from a roll-on dispenser which comprises about 5 to 40% by weight of an antiperspirant agent in the form of fine particles suspended in about 50 to 92% by weight of the composition of an anhydrous normally liquid medium by means of a suspending agent, and wherein:
   (i) the suspending agent comprises a hydrophobic clay in an amount of 3 to 15% by weight of the composition and
   (ii) the liquid medium consists of ethanol or isopropanol or mixture thereof and 0.5 C. % to about 3 C. % by weight of the total liquid medium of one or more liquids less volatile than ethanol, provided that where such other liquid comprises a nonpolar and water-immiscible liquid such nonpolar water-immiscible liquid is present in an amount of not more than about 2 C. % by weight of the total liquid phase, where C. is the percentage weight of the hydrophobic clay in the composition, provided also that when the amount of hydrophobic clay is less than 5% by weight then the composition comprises at least 66% by weight ethanol.

3. The antiperspirant composition according to claim 2 wherein the liquid medium consists of ethanol or isopropanol or mixtures thereof and from 0.5% C. to 1.5% C. by weight of the liquid medium of a nonpolar water-immiscible emollient oil.

4. The antiperspirant composition according to claim 2 wherein the composition comprises from 6 to 12% by weight of the hydrophobic clay and wherein the liquid medium consists of ethanol or isopropanol and from 0.5 C. % to 3.0 C. % by weight of the liquid medium of a hydrophillic emollient oil.

5. The antiperspirant composition according to claim 2 wherein the composition comprises from 6 to 12% by weight of the hydrophobic clay and wherein the liquid medium consists of ethanol or isopropanol and from 0.5 C. % to 2.0 C. % by weight of the liquid medium of a nonpolar water-immiscible emollient oil.

* * * * *